Figure 1:
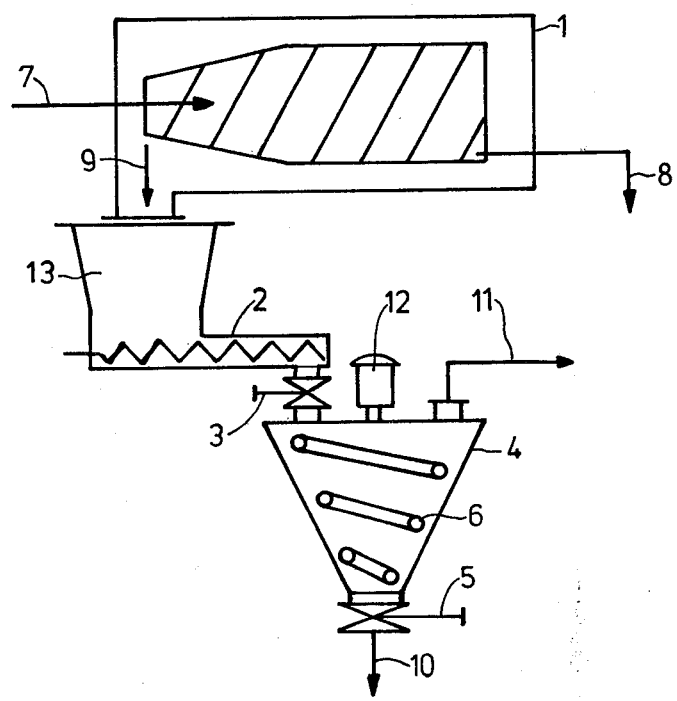

United States Patent [19]

Schaefer et al.

[11] 4,389,344

[45] Jun. 21, 1983

[54] PROCESS FOR SEPARATING SOLID 1,5- AND/OR 1,8-DINITROANTHRAQUINONE AND LIQUID NITROBENZENE

[75] Inventors: Axel Schaefer, Bonn; Werner Motika, Leverkusen; Wolfgang Bender, Burscheid; Jörn Todt, Leverkusen; Udo Oels, Krefeld, all of Fed. Rep. of Germany

[73] Assignee: Bayer Aktiengesellschaft, Leverkusen, Fed. Rep. of Germany

[21] Appl. No.: 99,115

[22] Filed: Nov. 29, 1979

[30] Foreign Application Priority Data

Dec. 16, 1978 [DE] Fed. Rep. of Germany ....... 2854427

[51] Int. Cl.³ ............................................ C07C 49/68
[52] U.S. Cl. ................................... 260/369; 159/2 R
[58] Field of Search ......................... 260/369; 203/88; 159/2 R

[56] References Cited

U.S. PATENT DOCUMENTS

| | | | |
|---|---|---|---|
| 3,836,547 | 9/1974 | Toth | 260/369 |
| 3,836,601 | 9/1974 | Frey et al. | 260/369 |
| 4,031,116 | 6/1977 | Thiem et al. | 260/369 |
| 4,076,734 | 2/1978 | Yamada et al. | 260/369 |

*Primary Examiner*—Charles F. Warren
*Assistant Examiner*—Raymond Covington
*Attorney, Agent, or Firm*—Sprung, Horn, Kramer & Woods

[57] ABSTRACT

A process and an equipment for obtaining dry 1,5- and-/or 1,8-dinitroanthraquinone from suspensions which contain liquid nitrobenzene whereby in a first stage solid 1,5- and/or 1,8-dinitroanthraquinone with a content of less than 30% by weight of nitrobenzene is separated off mechanically from the suspension at elevated temperature and whereby in a second stage the residued nitrobenzene is removed from the separated 1,5- and/or 1,8-dinitroanthraquinone by lowering the pressure during which the temperature falls.

8 Claims, 1 Drawing Figure

PROCESS FOR SEPARATING SOLID 1,5- AND/OR 1,8-DINITROANTHRAQUINONE AND LIQUID NITROBENZENE

In Ullmanns Enzyklopädie der technischen Chemie (Ullmann's Encyclopaedia of Industrial Chemistry), 3rd edition, volume 3, page 675 (1953) it is stated that when anthraquinone is dinitrated, mixtures which in each case contain about 40% of 1,5- and 1,8-dinitroanthraquinone about 20% of 1,6- and 1,7-dinitroanthraquinone and which are difficult to separate, are obtained. Various processes have been described according to which 1,5- and/or 1,8-dinitroanthraquinone can be separated off from crude mixtures of dinitroanthraquinones by means of nitrobenzene (see, for example, German Offenlegungsschriften (German Published Specifications) 2,248,704, 2,524,747 and 2,637,733 and Japanese Published Specification 49/76851). With these processes, suspensions of 1,5- and/or 1,8-dinitroanthraquinone in nitrobenzene are obtained at elevated temperature. The nitrobenzene then has to be removed from these suspensions, in order to obtain dry 1,5- and/or 1,8-dinitroanthraquinone.

A process for obtaining dry 1,5- and/or 1,8-dinitroanthraquinone from a suspension which contains solid 1,5- and/or 1,8-dinitroanthraquinone and liquid nitrobenzene has now been found which is characterised in that, in a first stage, solid 1,5- and/or 1,8-dinitroanthraquinone with a nitrobenzene content of less than 30% by weight is separated off mechanically from the suspension at elevated temperature and, in a second stage, the residual nitrobenzene is removed from the 1,5- and/or 1,8-dinitroanthraquinone which has been separated off, by lowering the pressure during which the temperature falls.

Any suspensions which contain liquid nitrobenzene and solid 1,5-dinitroanthraquinone or solid 1,8-dinitroanthraquinone or solid 1,5- and 1,8-dinitroanthraquinone can be employed in the process according to the invention. Preferably, these suspensions contain 2 to 200 g and especially 5 to 150 g of solid 1,5- and/or 1,8-dinitroanthraquinone, in each case based on 1 kg of liquid nitrobenzene. The suspension can also contain further 1,5- and/or 1,8-dinitroanthraquinone, as well as other compounds which are formed during the nitration of anthraquinone or mononitroanthraquinone, in the dissolved form in nitrobenzene. Suitable suspensions can, for example, be obtained from the working up of mixtures of dinitroanthraquinone in accordance with German Offenlegungsschrift (German Published Specification) 2,736,733.

According to the invention, a portion of the nitrobenzene is first separated off mechanically from the suspension employed. Conventional mechanical separating devices can be used for this purpose, for example filters or centrifuges, especially drum filters or screw centrifuges. A pressure drum filter is preferably used for the mechanical separation of nitrobenzene from suspensions containing solid 1,5-dinitroanthraquinone and a complete cage screw centrifuge is preferably used for the mechanical separation of nitrobenzene from suspensions containing solid 1,8-dinitroanthraquinone.

According to the invention, the mechanical separation is effected at elevated temperature. Suitable temperatures are, for example, those in the range of 80° to 150° C. The mechanical separation is preferably carried out at temperatures in the range of 90° to 130° C. Since suspensions which are at temperatures within the indicated ranges are obtained from the known processes for the separation of 1,5- and/or 1,8-dinitroanthraquinone from nitration mixtures by means of nitrobenzene, these suspensions can usually be employed direct, without cooling or warming, in the process according to the invention.

It is advantageous to carry out the mechanical separation at constant temperature. The device for the mechanical separation is therefore preferably fitted with a means of heating, to enable heat losses, for example due to radiation, to be compensated.

The mechanical separating device can also be so fitted out that washing of the solid 1,5- and/or 1,8-dinitroanthraquinone with nitrobenzene can also be carried out therein.

The mechanical separating off of nitrobenzene is carried out in such a way that residual, solid 1,5- and/or 1,8-dinitroanthraquinone contains less than 30% by weight and preferably less than 15% by weight of nitrobenzene. The liquid phase, and, where appropriate, the wash liquid, separated off in the mechanical separating device are removed. The dissolved constituents can be wholly or partly separated off from this phase if desired, for example by lowering the temperature or by evaporation.

In the second stage, the residual nitrobenzene is now removed, by lowering the pressure as the temperature falls, from the solid 1,5- and/or 1,8-dinitroanthraquinone which has been separated off in the mechanical separating device and which still contains residual nitrobenzene. The procedure here can be to introduce the product from the first stage at elevated temperature into a vessel to which a vacuum can be applied and to apply a vacuum to this vessel without the external supply of heat. Nitrobenzene still adhering to the 1,5- and/or 1,8-dinitroanthraquinone then vaporises with cooling of the 1,5- and/or 1,8-dinitroanthraquinone. Drying proceeds more rapidly and more completely the more rapidly the pressure in the vessel to which a vacuum can be applied is lowered and the greater the lowering of the pressure. In general, it suffices if the pressure is lowered to 0.2 to 30 mbars. Preferably, the pressure is lowered to 1 to 20 mbars. Under these pressures it is possible, without any special effort, to collect the vaporised nitrobenzene in front of the vacuum pump, for example by condensation.

The temperature of the product before the pressure is lowered is usually the same as that at which the product is obtained from the stage in which nitrobenzene is separated off mechanically. In some cases, however, it can be advantageous to bring the product to a higher temperature before lowering the pressure. For example, this is advantageous if the residual moisture content prior to lowering the pressure is relatively high, if the lowering of the pressure is relatively slight and/or if the temperature prior to lowering the pressure is relatively low.

If the temperature is raised, this is effected to at most a few degrees below the boiling point of nitrobenzene under normal pressure. For example, the product from the stage in which nitrobenzene is separated off mechanically can be introduced into the second stage at a temperature of 80° to 205° C. or 90° to 190° C. Particularly preferentially, the product from the stage in which nitrobenzene is separated off mechanically is introduced into the second stage of the process at the temperature at which it is obtained after nitrobenzene has been separated off mechanically.

As the pressure is lowered, the temperature of the solid 1,5- and/or 1,8-dinitroanthraquinone falls at the same rate as nitrobenzene vaporises. Drying generally takes place to residual nitrobenzene contents of less than 1% by weight and preferably of less than 0.5% by weight. The dried product then generally has a temperature in the range of 15° to 130° C. and preferably 40° to 95° C. The dried product, after cooling if appropriate, can then be packed and stored or used direct for further reactions.

A vessel to which a vacuum can be applied, and in which the second stage of the process according to the invention can be carried out, can be of any desired construction. In general it is fixed and contains no devices for mechanical mixing during the application of the vacuum. Preferably, the vessel is so constructed that the dried product can be withdrawn in a simple and rapid manner, for example at the base. For this purpose, it can be advantageous to provide the vessel with a stirrer which has a gentle action. In order to prevent possible condensation of nitrobenzene on the walls of the vessel, it can be advantageous to design these walls so that they can be heated. The drying time is in general very short, since usually a residual content of nitrobenzene of less than 1% by weight and preferably less than 0.5% by weight already exists when the final pressure is obtained on application of the vacuum. The formation of dust during the application of the vacuum is not observed, so that filtering off the vapours is not necessary and a free-flowing product is obtained. The dried product is preferably withdrawn from the vessel after admitting air into the latter.

The second stage of the process according to the invention is preferably operated quasi-continuously, by providing a buffer space upstream of the vessel to which a vacuum can be applied and allowing the steps "filling of the vessel", "application of a vacuum to the vessel", "admission of air into the vessel" and "emptying of the vessel" to proceed in rapid succession in a continuous cycle.

In a preferred embodiment of the process according to the invention a metering device, which is connected by means of a vacuum-tight shut-off device to the vessel to which a vacuum can be applied, is located between the first and second stages. The metering device can be of various constructions. A screw is preferably used. The metering device is preferably heatable. By means of the heater, it is possible either to compensate for heat loss, for example due to radiation, or, if desired, to produce a previously described rise in the temperature of the product from the mechanical separation. The rise in temperature can optionally also be produced by warming the vessel to which a vacuum can be applied, before or during filling. The vacuum-tight shut-off device can be of any design, for example in the form of a slide valve.

In a preferred industrial embodiment of the process according to the invention, the procedure is as follows: the starting suspension of solid 1,5- and/or 1,8-dinitroanthraquinone in liquid nitrobenzene is fed at a temperature in the range of 80° to 150° C. into a pressure drum filter or a complete cage screw centrifuge, in which liquid nitrobenzene is continuously separated off mechanically at constant temperature and a product containing less than 30% by weight of nitrobenzene is obtained continuously. A wash with nitrobenzene is optionally also carried out in the pressure drum filter or the complete cage screw centrifuge. The nitrobenzene separated off is removed. The product is discharged into a buffer space, from which it is fed via a heatable screw and a vacuum-tight slide valve into a vessel to which a vacuum can be applied. By means of the screw, a specific amount of the product, the temperature of which is the same as or higher than that of the product after separating off nitrobenzene mechanically, is metered into the vessel. After shutting off the screw, the slide valve is closed and a vacuum is applied to the vessel. The nitrobenzene which vaporises is separated off upstream of the vacuum pump. After a final pressure of 0.2 to 30 mbars has been reached, air is admitted into the vessel and the vessel is emptied. The cycle then starts again.

A particularly preferred industrial embodiment of the process according to the invention is explained below with the aid of FIG. 1:

A solid nitrobenzene suspension (7) containing 1,5- or 1,8-dinitroanthraquinone is fed into a mechanical separating device (1). Liquid nitrobenzene is removed via (8) and pre-dried 1,5- or 1,8-dinitroanthraquinone with a maximum residual moisture content of 30% by weight (9) is discharged into the buffer vessel (13). The pre-dried product is metered via the screw (2) and the shut-off device (3) into the vessel (4) to which a vacuum can be applied. After metering has ended, the screw (2) is shut off, the shut-off device (3) is closed and a vacuum is applied to the vessel (4) via line (11) until a final pressure of 1 to 20 mbars is reached. After the final pressure has been reached, air is admitted into the vessel (4) and the vessel is emptied with the aid of the stirrer (12) through the outlet (10). The temperature of the solid 1,5- or 1,8-dinitroanthraquinone is kept in the range of 90° to 100° C. until nitrobenzene has been removed in vacuo.

The present invention also relates to equipment for removing nitrobenzene from suspensions which contain solid 1,5- and/or 1,8-dinitroanthraquinone and nitrobenzene, which is characterised in that it consists of a mechanical separating device (1) and a vessel (4) to which a vacuum can be applied. Preferably, the mechanical separating device (1) is a pressure drum filter or a complete cage screw centrifuge and the vessel (4) to which a vacuum can be applied is provided with an outlet device (5) at the base and with a stirrer (12) in order to facilitate emptying.

The process according to the invention and the equipment according to the invention have a number of advantages. Thus, the heat of the solid in the suspension is utilised to vaporise the nitrobenzene and a supply of heat during drying is not necessary. Even if the metering device and/or the vessel to which a vacuum can be applied are heated, only very small amounts of heat are required for this purpose. Furthermore, no dust fractions form during drying so that a free-flowing, non-dusting product forms and devices for filtering the vapours can be dispensed with. Because of the short times which are required for drying, the vessel to which a vacuum can be applied can be relatively small. The dried product is generally obtained at a low temperature, so that usually it can be packed and stored, or used for further reactions, in the form in which it is obtained or, if cooling is necessary, only moderate subsequent cooling is required.

It is surprising that the drying according to the invention results in success in such a simple manner. Conventional vacuum driers start with drying at relatively low temperatures and the removal of the final residues of moisture is facilitated by heating during drying. With the process according to the invention, the temperature pattern is precisely the reverse, that is to say, the final residues of moisture are removed at the lowest temperature. Nevertheless, a dry product is obtained within a short time. Furthermore, with conventional vacuum driers the dry material is mixed mechanically (tumbler drier, paddle drier) in order to improve the heat transfer to the product and to facilitate the diffusion of moisture out of the solid particles. No provision is made for mechanical mixing of this type in the process according to the invention during drying in vacuo. Nevertheless, a dry product is obtained within a short time.

EXAMPLES

EXAMPLE 1 (SEE ALSO FIG. 1)

The separation of 150 kg of 1,8-dinitroanthraquinone per hour from a mixture of dinitroanthraquinone isomers is effected by crystallisation in nitrobenzene. A suspension is obtained which contains 15 g of solid 1,8-dinitroanthraquinone per kg of the suspension. The suspension is at a temperature of 107° C. In addition to nitrobenzene, the liquid phase of the suspension contains isomeric dinitroanthraquinones in the dissolved form.

This suspension (7) is fed to a heated complete cage screw centrifuge (1). A large proportion of the liquid phase is removed from the suspension in this centrifuge and let off via (8). The solid 1,8-dinitroanthraquinone is obtained with a residual moisture content of 9% by weight (9). This product is fed at a temperature of 107° C. into a buffer vessel (13) and from there is fed via a metering screw (2) and a vacuum-tight slide valve (3) into a vessel (4) to which a vacuum can be applied. The vessel to which a vacuum can be applied is operated with a cycle time of 30 minutes and has a capacity of 200 dm³. After filling, the metering screw (2) is shut off and the slide valve (3) is closed. A vacuum is then applied to the vessel via line (11) until a vacuum of 5 mbars is obtained.

The 1,8-dinitroanthraquinone dries, without dusting, to residual moisture contents of less than 0.5% by weight and during drying cools to 70° C. After the pressure of 5 mbars has been reached, air is admitted to the vessel (4) and the dried 1,8-dinitroanthraquinone (10) is discharged with the aid of the stirrer (12) through the outlet (5).

EXAMPLE 2 (SEE ALSO FIG. 1)

500 kg of 1,5-dinitroanthraquinone per hour are separated off from a mixture of dinitroanthraquinone isomers by crystallisation in nitrobenzene. The hot suspension, which is at 115° C., contains 110 g of solid 1,5-dinitroanthraquinone per kg of suspension. In addition to nitrobenzene, the liquid phase of the suspension contains isomeric dinitroanthraquinones in the dissolved form. This suspension is fed via (7) into a pressure drum filter (1). The major proportion of the liquid phase is separated off (8) in a pressure drum filter. After the mechanical removal of moisture, the solid 1,5-dinitroanthraquinone (9) has a residual moisture content of 15% by weight and is fed via a small buffer vessel (13) through a metering screw (2) into a vessel (6) to which a vacuum can be applied. The cycle time is 30 minutes and the vessel has a capacity of about 600 dm³. During filling of the vessel, the moist material is warmed to 150° C. by the walls of the metering device (2), which are heated to 180° C. As in Example 1, after filling, the metering screw is shut off and the vessel is shut off and a vacuum is applied. The 1,5-dinitroanthraquinone dries to final moisture contents of less than 0.5% and during drying cools to 60° to 70° C. After the pressure of 5 mbars has been reached, air is admitted to the vessel and the dried 1,5-dinitroanthraquinone (10) is discharged with the aid of a stirrer (12) through the outlet pipe (5), which can be shut off.

What is claimed is:

1. A process for obtaining dry 1,5- and/or 1,8-dinitroanthraquinone from suspensions which contain solid 1,5- and/or 1,8-dinitroanthraquinone and liquid nitrobenzene, comprising separating off mechanically from the suspension at elevated temperature in a first stage, solid 1,5- and/or 1,8-dinitroanthraquinone with a nitrobenzene content of less than 30% by weight and removing in a second stage, the residual nitrobenzene from the 1,5- and/or 1,8-dinitroanthraquinone which has been separated off, by lowering the pressure during which the temperature falls.

2. The process of claim 1, wherein the first stage is carried out at 80° to 150° C.

3. The process of claim 1, wherein prior to lowering the pressure, the product is brought to a temperature of 80° to 205° C.

4. The process of claim 1, wherein the pressure is lowered to 0.2 to 30 mbars.

5. The process of claim 1, wherein no mechanical mixing is carried out during lowering of the pressure.

6. The process of claim 1, wherein the product from the first stage is fed into the second stage via a heatable metering device and a vacuum-tight shut-off device.

7. The process of claim 1, wherein the first stage is carried out continuously and the second stage is carried out quasi-continuously.

8. The process of claim 7, wherein a buffer space is located upstream of the second stage.

* * * * *